(12) United States Patent
Cho et al.

(10) Patent No.: US 10,772,200 B2
(45) Date of Patent: Sep. 8, 2020

(54) FABRIC COATED WITH FUNCTIONAL SILICONE RUBBER

(71) Applicant: WAVE COMPANY CO., LTD., Seoul (KR)

(72) Inventors: Na-Yun Cho, Seoul (KR); Sang-Chul Lee, Seoul (KR); Ji-Hun Han, Seoul (KR)

(73) Assignee: WAVE COMPANY CO., LTD. (KR)

( * ) Notice: Subject to any disclaimer, the term of this patent is extended or adjusted under 35 U.S.C. 154(b) by 114 days.

(21) Appl. No.: 16/199,379

(22) Filed: Nov. 26, 2018

(65) Prior Publication Data

US 2019/0208629 A1 Jul. 4, 2019

(30) Foreign Application Priority Data

Dec. 28, 2017 (KR) .................. 10-2017-0182987
Jul. 9, 2018 (KR) .................. 10-2018-0079650

(51) Int. Cl.
*D06N 3/00* (2006.01)
*H05K 1/03* (2006.01)
(Continued)

(52) U.S. Cl.
CPC .......... *H05K 1/095* (2013.01); *A61N 1/0484* (2013.01); *D06N 3/0006* (2013.01); *D06N 3/0063* (2013.01); *D06N 3/128* (2013.01); *H05K 1/0283* (2013.01); *H05K 1/038* (2013.01); *D06N 2203/066* (2013.01); *D06N 2205/02* (2013.01); *D06N 2209/041* (2013.01);
(Continued)

(58) Field of Classification Search
CPC ........................ H05K 9/009; H05K 9/0006
See application file for complete search history.

(56) References Cited

U.S. PATENT DOCUMENTS

| | | | |
|---|---|---|---|
| 6,222,126 B1 * | 4/2001 | Strange ............. | H01R 13/2492 174/393 |
| 2005/0029000 A1 * | 2/2005 | Aisenbrey ............... | H01B 1/22 174/388 |

(Continued)

FOREIGN PATENT DOCUMENTS

| | | |
|---|---|---|
| KR | 10-2016-0092575 A | 8/2016 |
| KR | 10-1693306 B1 | 1/2017 |
| KR | 10-2018-0032457 A | 3/2018 |

*Primary Examiner* — Hung V Ngo
(74) *Attorney, Agent, or Firm* — Park & Associates IP Law, P.C.

(57) ABSTRACT

A fabric coated with functional silicone rubber, the fabric being configured such that a coating layer may not be easily separated from the fabric and may be used to form a power line or a signal line. The fabric includes: a woven fabric made by weaving and including uniform pores therein; and a coating layer formed by coating a surface of the woven fabric with liquid silicone rubber in which electrically conductive particles larger than the pores of the woven fabric are dispersed and mixed, wherein the liquid silicone rubber permeates into the pores of the woven fabric by the weight thereof and is cured such that the silicone rubber is anchored to the woven fabric, and an electrically conductive layer having electrical conductivity is formed as the electrically conductive particles are caught on the surface of the woven fabric and increase in density at the surface of the woven fabric.

9 Claims, 6 Drawing Sheets (51) Int. Cl.
*H05K 1/09* (2006.01)
*H05K 1/02* (2006.01)
*A61N 1/04* (2006.01)
*D06N 3/12* (2006.01)

(52) U.S. Cl.
CPC ...... *D06N 2211/10* (2013.01); *D10B 2501/02* (2013.01); *D10B 2509/00* (2013.01); *H05K 2201/0116* (2013.01); *H05K 2201/0162* (2013.01); *H05K 2201/0314* (2013.01); *H05K 2201/0391* (2013.01)

(56) References Cited

U.S. PATENT DOCUMENTS

| | | | |
|---|---|---|---|
| 2014/0272351 A1* | 9/2014 | Creasy, Jr. | H05K 9/009 |
| | | | 428/215 |
| 2017/0086513 A1* | 3/2017 | Maxey | A41H 43/04 |
| 2019/0053372 A1* | 2/2019 | Kwon | H05K 1/185 |

* cited by examiner

FABRIC COATED WITH FUNCTIONAL SILICONE RUBBER

REFERENCE TO RELATED APPLICATIONS

This application claims the priority benefit of Korean Patent Application No. 10-2017-0182987 filed on Dec. 28, 2017 and Korean Patent Application No. 10-2018-0079650 filed on Jul. 9, 2018, the entire contents of which are incorporated herein by reference.

FIELD OF THE INVENTION

The present invention relates to a fabric coated with functional silicone rubber, and more particularly, to a technique for preventing separation of a coating layer formed on a fabric and minimizing variations in electrical conductivity.

BACKGROUND OF THE INVENTION

In electrical stimulation therapy (EST), the contraction of muscle is artificially induced by electrical signals.

Electrical muscle stimulation (EMS), a kind of EST, is a training tool used for athletes or ordinary people to help patients who can not move their body parts or whole bodies to recover or not to suffer from secondary symptoms, or to help athletes to recover after exercise.

In recent years, EMS has also been used for beauty purposes in addition to training and treatment purposes. Since the effect of correcting the body shape can be obtained by strengthening muscle, EMS is being increasingly introduced into the field of training for beauty purposes and is also highly effective in obtaining an additional effect of calorie consumption.

In the related art, patch type devices are mainly used for EMS. However, it is difficult to carry such a patch type device having a large oscillator, thereby limiting places where a user can exercise after attaching patches thereto. In addition, as the number of body parts to which patches are attached increases, the number of electric wires for connecting an oscillator to the patches increases, thereby limiting exercise.

To address these problems, the inventors of the present invention have proposed a functional garment for electrical stimulation in Korean Patent Application No. 2016-0121727.

In the disclosed technique, power lines are formed on a garment fabric by coating the garment fabric with electrically conductive liquid silicone rubber containing electrically conductive particles of, for example, copper or silver, and curing the electrically conductive liquid silicone rubber.

Since the power lines are based on silicone rubber, the power lines are flexible when a user wearing the functional garment exercises or moves, thereby maintaining their power line function. However, the electrical conductivity of the power lines varies as the power lines expand and contract.

The reason for this is as follows: since the electrically conductive particles dispersed in the silicone rubber generally have a spherical shape, the density of the electrically conductive particles is uniform before the power lines are stretched but is varied when the power lines are stretched, causing variations in the electrical conductivity of the power lines. In particular, if the density of the electrically conductive particles becomes very low at a particular portion when the power lines are stretched, the supply of power may be interrupted due to the particular portion, and thus the power lines may not function as power lines.

In addition, it is necessary to form an additional insulative film on the power lines to prevent a wearer from being exposed to the power lines, and thus an additional process has to be performed to form the insulative film.

In addition, if external force such as rubbing force is applied to the power lines, the silicone rubber coating may be easily separated and damaged.

SUMMARY OF THE INVENTION

An object of the present invention is to provide a fabric coated with functional silicone rubber and configured to minimize variations in electrical conductivity even when the fabric for garments is stretched as a wearer moves.

Another object of the present invention is to provide a fabric coated with functional silicone rubber in such a manner that the functional silicone rubber is not easily separated from the fabric by external force.

Another object of the present invention is to provide a fabric coated with functional silicone rubber in such a manner that power connection is not interrupted even when a garment made of the fabric is stretched as a wearer moves.

According to an aspect of the present invention, there is provided a fabric coated with functional silicone rubber, the fabric including: a woven fabric made by weaving and including uniform pores therein; and a coating layer formed by coating a surface of the woven fabric with liquid silicone rubber in which electrically conductive particles larger than the pores of the woven fabric are dispersed and mixed, wherein the liquid silicone rubber permeates into the pores of the woven fabric by the weight thereof and is cured such that the silicone rubber is anchored and coupled to the woven fabric, and an electrically conductive layer having electrical conductivity is formed as the electrically conductive particles are caught on the pores of the woven fabric at an interface with the woven fabric and increase in density at the interface.

The coating layer may be formed by dispersing and mixing electrically conductive wires together with the electrically conductive particles in the liquid silicone rubber and curing the liquid silicone rubber.

The electrically conductive wires may have elasticity and restoring force in a length direction thereof and may be irregularly tangled with each other in the silicone rubber.

The electrically conductive wires may include an electrically conductive fiber and electrically conductive fine metal wires and may have a spring shape having gaps between turns, a zigzag shape, or a hook shape.

The electrically conductive wires may have a single fiber, wool, or mesh structure.

As the electrically conductive particles move downward in the coating layer, the electrically conductive particles gradually decrease in density in a direction from the interface with the woven fabric toward a surface of the coating layer such that the surface of the coating layer has no or low electrical conductivity.

The electrically conductive particles may have uniform density as a whole up to a surface of the coating layer in a thickness direction of the coating layer except for the electrically conductive layer such that the surface of the coating layer has electrical conductivity.

An electrically conductive electrode may be formed by coating the surface of the coating layer with electrically conductive liquid silicone rubber in which carbon powder is dispersed and mixed, and curing the electrically conductive liquid silicone rubber.

According to the above-described structure, a lower surface of the coating layer may be stuck and fixed to the woven fabric by anchoring, and thus even when the coating layer is rubbed, the coating layer may not be separated.

In addition, since the upper surface of the coating layer is not electrically conductive, it is not necessary to form an additional insulative film on the coating layer. That is, a process required in the related art for forming an additional insulative film on the coating layer is not necessary.

In addition, since the electrically conductive wires having elasticity and restoring force are tangled with each other, even when the fabric is stretched as a wearer moves, variations in electrical conductivity may be minimized.

In addition, since the electrically conductive wires can absorb stretching of the coating layer, electrical disconnection at a particular portion may be prevented.

In addition, since the electrically conductive layer is buried in the coating layer, although the surface of the coating layer is partially broken or damaged, a power line may not be cut, and variations in electrical conductivity may be minimized.

BRIEF DESCRIPTION OF THE DRAWINGS

The above objects and other advantages of the present invention will become more apparent by describing in detail exemplary embodiments thereof with reference to the attached drawings in which.

DETAILED DESCRIPTION OF THE INVENTION

Hereinafter, specific embodiments of the present invention will be described in detail with reference to the accompanying drawings.

Figure 1:
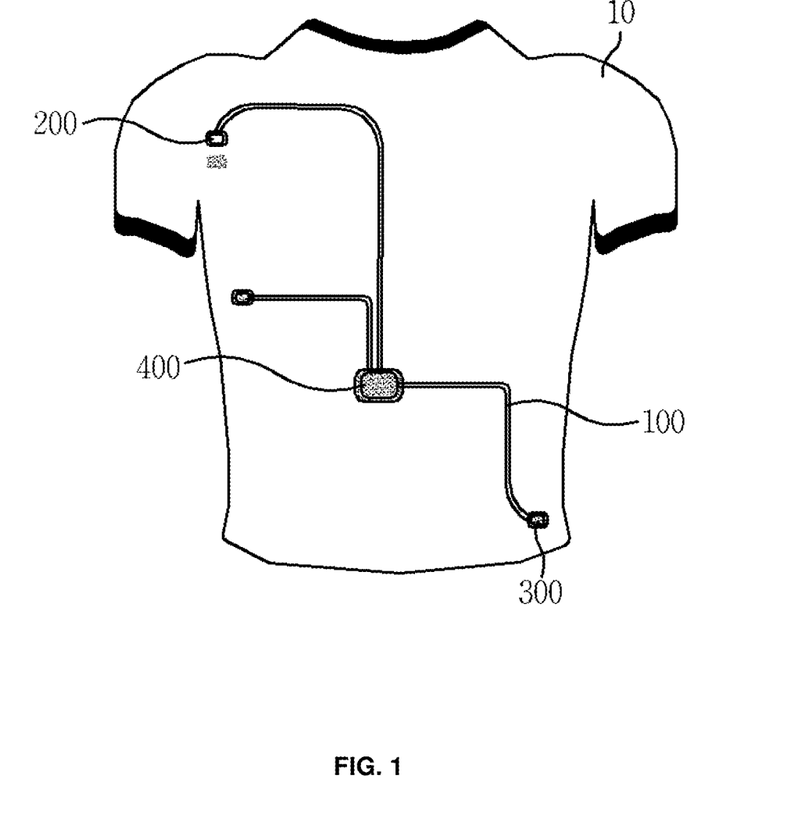
FIG. 1 is a view illustrating a functional garment for electrical stimulation according to the present invention.
Figure 2:
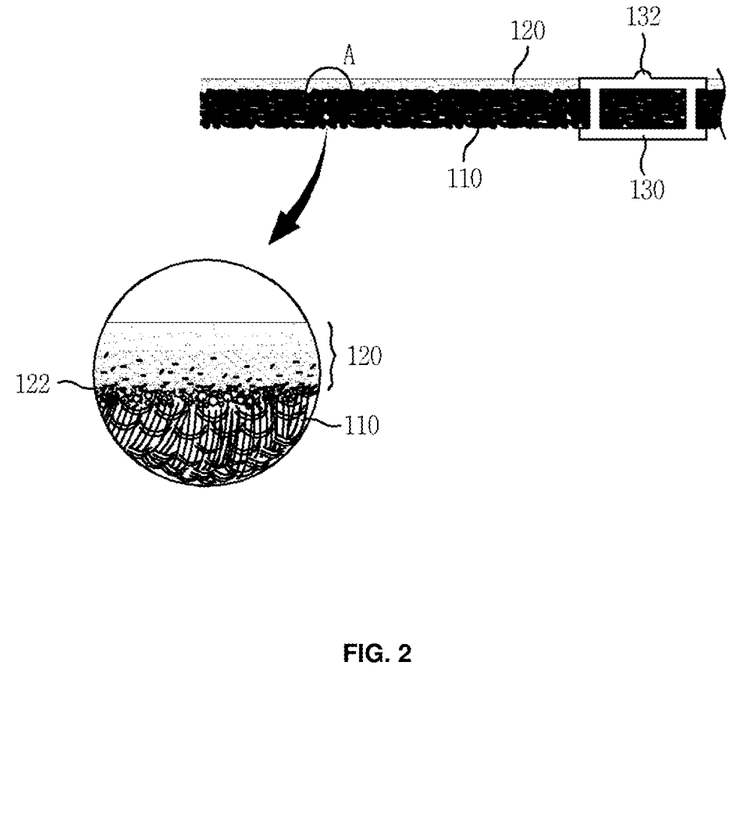
FIG. 2 is a cross-sectional view taken along line 2-2 in FIG. 1 for illustrating a fabric coated with functional silicone rubber according to an embodiment of the present invention.
Figure 3:
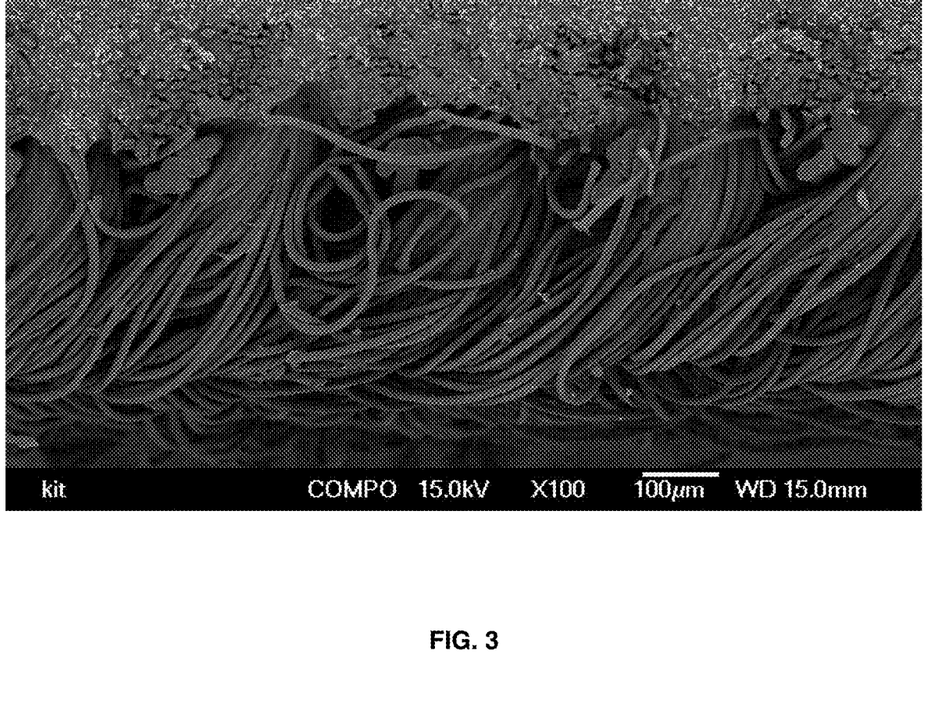
FIG. 3 is a scanning electron microscope (SEM) image of the fabric coated with functional silicone rubber.

FIG. 1 is a view illustrating a functional garment for electrical stimulation according to the present invention, FIG. 2 is a cross-sectional view taken along line 2-2 in FIG. 1, and FIG. 3 is a scanning electron microscope (SEM) image of the fabric coated with functional silicone rubber.

A plurality of electric lines 100 are coated in a line pattern on an outer surface of a garment fabric 10 such as a T-shirt fabric, and a sensor 200, a measuring device 300, and a controller 400 are detachably attached to end portions of the electric lines 100, thereby providing a smart garment.

Herein, the sensor 200 is a motion recognition sensor, the measuring device 300 is a small device for measuring a pulse rate or oxygen saturation, and the controller 400 is a control module for receiving signals from the sensor 200 and the measuring device 300 and wirelessly transmitting the signals to a remote place.

Referring to FIG. 2, each of the electric lines 100 is formed by a silicone rubber coating layer 120 formed on an outer surface of a woven fabric 110. In addition, an electrode terminal such as a snap button 130 may be inserted through the woven fabric 110 and the coating layer 120, and owing to a protrusion 132 formed on the snap button 130, an external device such as the sensor 200, the measuring device 300, the controller 400 may be electrically and mechanically attached and detached.

In this case, a portion of the snap button 130 may be located inside the woven fabric 110 and make contact with the skin of a wearer to transmit measured information to the sensor 200 or the measuring device 300.

Although not shown in FIGS. 1 to 3, a self-adhesive layer may be formed in a predetermined pattern on an inner surface of the woven fabric 110, and may make contact with the skin of a wearer and pull the skin upward by self-adhesion to provide a muscle taping effect.

The coating layer 120 may be formed by coating the woven fabric 110 with electrically conductive liquid silicone rubber containing electrically conductive particles or powder of, for example, copper, silver, aluminum, or nickel, and curing the liquid silicone rubber.

The coating layer 120 may be formed by curing the liquid silicone rubber in which the electrically conductive particles are mixed with electrically conductive wires.

As the liquid silicone rubber is cured in a state in which the electrically conductive wires are mechanically and electrically tangled and connected to each other at least in a length direction thereof, the positions of the electrically conductive wires are determined in the coating layer 120.

Herein, the electrically conductive wires may have any shapes and materials as long as the electrically conductive wires are electrically conductive and have elasticity and restoring force in the length direction thereof and can be tangled. For example, the electrically conductive wires may include an electrically conductive fiber or fine metal wires.

The electrically conductive fiber may be single fiber, wool, or mesh. In particular, when the electrically conductive fiber is single fiber, the electrically conductive fiber may have a spring shape, a zigzag shape, or a hook shape as shown in FIGS. 4A to 4C.

Figure 4A:
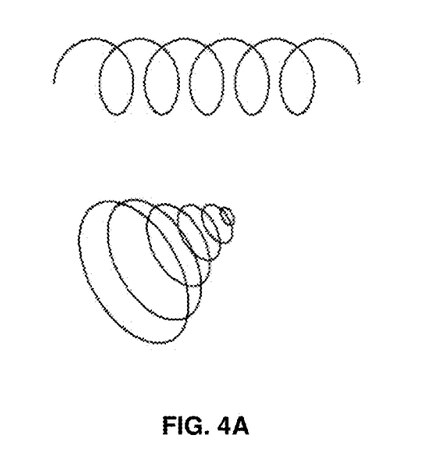
FIGS. 4A to 4C are views illustrating shapes of electrically conductive wires.

As shown in FIG. 4A, the electrically conductive wires may have a spring shape having elasticity and restoring force in the length direction thereof and may have a constant diameter or an increasing or decreasing diameter. In particular, if gaps are formed between turns in the spring shape, end portions of adjacent spring fiber threads may be inserted into the gaps and may be tangled, thereby forming mechanically secure electrical coupling.

Figure 4B:
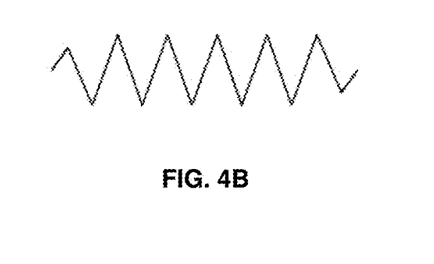

Referring to FIG. 4B, the electrically conductive wires may have a zigzag shape having elasticity and restoring force in the length direction thereof. Like spring wires, the electrically conductive wires having a zigzag shape are mechanically and electrically coupled to each other as the electrically conductive wires are tangled with each other and coupled to each other.

Figure 4C:
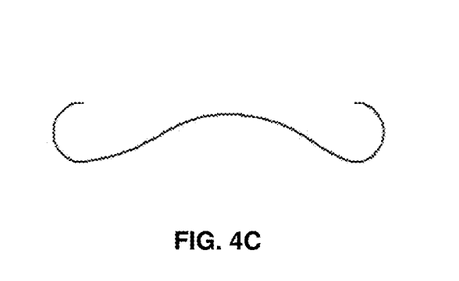

Referring to FIG. 4C, the electrically conductive wires may have a hook shape and may be mechanically and electrically connected to each other as electrically conductive wires adjacent to each other in the length direction thereof are coupled to each other at both ends thereof. In particular, when the electrically conductive wires are stretched, curved middle sections of the electrically conductive wires may sufficiently manage the stretching, and the hook shape of the electrically conductive wires may prevent separation of the electrically conductive wires.

The electrically conductive wires may be fine metal wires such as fine copper wires or may be in the form of copper wool or copper mesh.

Since the electrically conductive wires are not easily separated from each other owing to the tangled structure thereof, electrical conductivity may be improved compared to the case in which only electrically conductive particles are mixed in the coating layer 120, and particularly when the coating layer 120 is stretched as the garment is stretched, electrical conductivity may little vary because the electrically conductive wires are tangled with each other and have elasticity and restoring force in the length direction thereof, thereby preventing interruption of electric power.

Referring to the enlarged circle in FIG. 2, the electrically conductive particles are dense at the interface between the woven fabric 110 and the coating layer 120, thereby forming an electrically conductive layer 122.

The woven fabric 110 may be formed by weaving and may thus have uniform pores therein, and in FIG. 2, portions of weft and warp are shown.

The electrically conductive particles or the electrically conductive wires of the coating layer 120 are larger than the pores of the woven fabric 110, and when the liquid silicone rubber in which the electrically conductive particles or the electrically conductive wires are dispersed is cast onto a surface of the woven fabric 110, the liquid silicone rubber permeates into the pores of the woven fabric 110.

If the liquid silicone rubber is cured in this state, portions of the coating layer 120 are stuck in the pores of the woven fabric 110 by anchoring, thereby enhancing the coupling between the coating layer 120 and the woven fabric 110. As a result, although the coating layer 120 is rubbed, the coating layer 120 is not easily separated.

In addition, the electrically conductive particles and the electrically conductive wires dispersed in the liquid silicone rubber move downward in the coating layer 120 because of their weights, and since the electrically conductive particles and the electrically conductive wires are larger than the pores of the woven fabric 110, the electrically conductive particles and the electrically conductive wires are not inserted into the pores but are caught on the surface of the woven fabric 110.

As a result, the density of the electrically conductive particles and the electrically conductive wires is relatively high at the interface between the coating layer 120 and the woven fabric 110, and as curing occurs in this state, the electrically conductive layer 122 is formed by the silicone rubber and the electrically conductive particles and wires caught on the surface of the woven fabric 110.

On the contrary, since the electrically conductive particles and the electrically conductive wires move downward in the coating layer 120, the density of the electrically conductive particles and the electrically conductive wires decreases in a direction from the interface between the woven fabric 110 and the coating layer 120 toward a surface of the coating layer 120, and thus the surface of the coating layer 120 has no or very low electrical conductivity.

Therefore, since the surface of the coating layer 120 has no or very low electrical conductivity, it is not necessary to form an additional insulative film on the coating layer 120. That is, an additional process used in the related to form an insulative film on an electrically conductive coating layer is not necessary.

In addition, since the electrically conductive layer 122 is formed between the woven fabric 110 and the coating layer 120 instead of being formed on the surface of the coating layer 120, that is, the electrically conductive layer 122 is buried in the coating layer 120, even if the surface of the coating layer 120 is partially broken or damaged, the electric line 100 may not be cut or may be minimally varies in electrical conductivity.

Figure 5:
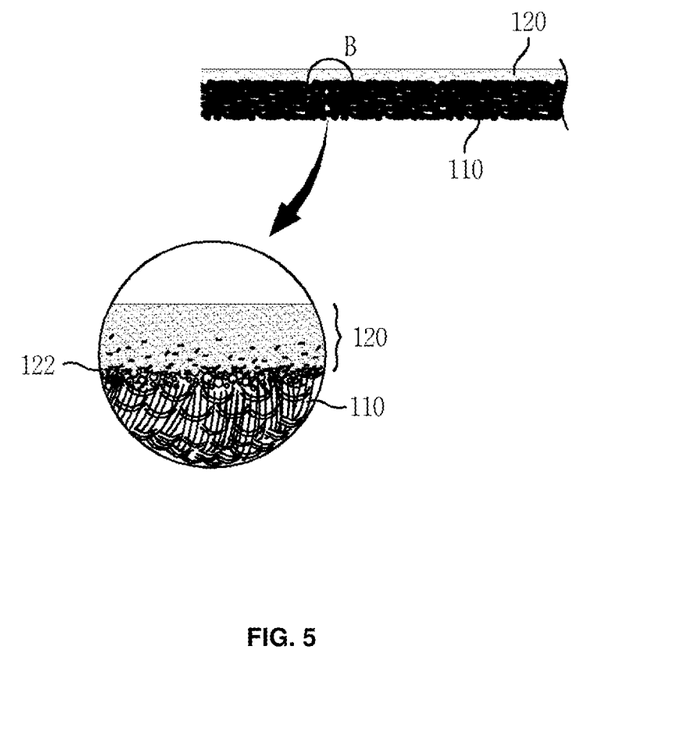
FIG. 5 is a cross-sectional view illustrating a fabric coated with functional silicone rubber according to another embodiment of the present invention.

FIG. 5 is a cross-sectional view illustrating a fabric coated with functional silicone rubber according to another embodiment of the present invention.

In the current embodiment, as shown in the circle in FIG. 5, the density of electrically conductive particles is uniform as a whole in the thickness direction of a coating layer 120 except for an electrically conductive layer 122, and thus the surface of the coating layer 120 is electrically conductive.

For example, if electrically conductive liquid silicone rubber containing electrically conductive wires and electrically conductive particles or powder of, for example, copper, silver, aluminum, or nickel is coated on a base film such as a release film and is then left for a predetermined time, the electrically conductive particles having a specific gravity move downward by their own weight and gather at the interface with the base film before the electrically conductive liquid silicone rubber is cured. As a result, the density of the electrically conductive particles increases at the interface with the base film.

Thereafter, the base film is turned upside down such that the uncured electrically conductive liquid silicone rubber may face and make contact with a woven fabric 110, and then a constant pressure is applied to the base film.

As a result, the electrically conductive particles densely distributed at the interface with the base film may move downward by their own weight to form the electrically conductive layer 122 on the boundary with the woven fabric 110. Therefore, unlike the previous embodiment, since the density of the electrically conductive particles has already increased at the surface of the coating layer 120, although the electrically conductive particles move downward, the density of the electrically conductive particles at the surface of the coating layer 120 may be maintained at a certain level.

If curing occurs in this state, as shown in FIG. 5, the electrically conductive layer 122 is formed on the boundary between the coating layer 120 and the woven fabric 110, and the density of the electrically conductive particles is uniform as a whole up to the surface of the coating layer 120 in the thickness direction of the coating layer 120. Thus, the surface of the coating layer 120 is electrically conductive.

If the coating layer 120 having an electrically conductivity surface is formed in this manner, various applications are possible in addition to use as electrical lines.

Figure 6A:
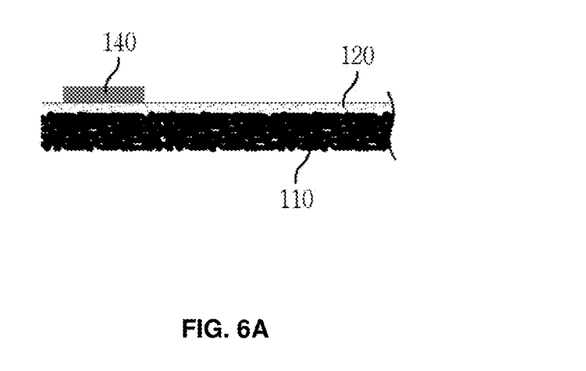
FIGS. 6A and 6B are views illustrating application examples of the fabric coated with functional silicone rubber of the embodiment shown in FIG. 5.
Figure 6B:
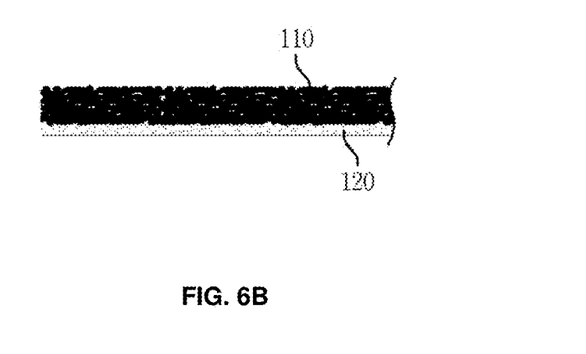

FIGS. 6A and 6B are views illustrating application examples of the fabric coated with functional silicone rubber of the embodiment shown in FIG. 5.

Referring to FIG. 6A, if an electrode 140 is formed on the coating layer 120 and power is applied to the electrode 140 from the outside, since the coating layer 120 is conductive in the thickness thereof, power may be supplied to the electrically conductive layer 122.

The electrode 140 may be formed by coating the coating layer 120 with electrically conductive liquid silicone rubber in which electrically conductive particles such as carbon powder are dispersed and mixed, and curing the electrically conductive liquid silicone rubber.

The content of the carbon powder which is a conductive filler may be decreased to increase the durability of the electrode 140 coated with carbon, and the thickness of the electrode 140 may be decreased to offset a corresponding increase in the resistance of the electrode 140. In this case, the electrode 140 may be used as an anisotropic conductive layer.

Since the electrode 140 containing carbon is highly durable, inexpensive, resistant to oxidation, and harmless to humans, the electrode 140 may be used as an electrode making contact with a sensor or a measuring device of a functional garment for electrical stimulation.

In addition, referring to FIG. 6B, when the fabric is used for a globe to which a stimulator is attached for virtual reality (VR) or augmented reality (AR), the surface of the coating layer 120 may be in contact with the skin of a wearer to transmit signals from the stimulator to the skin, and the electrically conductive layer 122 may be used as a power line.

In addition, if an electrocardiogram sensor or an electromyography sensor is used instead of the stimulator, the coating layer 120 may be used as a bio-electrode for reading electrocardiogram signals or electromyography signals.

Those of ordinary skill in the art may make changes or modifications from the above description without departing from the spirit and scope of the present invention. Therefore, the embodiments of the present invention are for illustrative purposes only and are not intended to limit the scope of the present invention. The scope of the present invention should be construed according to the appended claims, and it should be understood that all technical ideas equivalent to those described above are within the scope of the present invention.

What is claimed is:

1. A fabric coated with functional silicone rubber, the fabric comprising:
    a woven fabric made by weaving and comprising uniform pores therein; and
    a coating layer formed by coating a surface of the woven fabric with liquid silicone rubber in which electrically conductive particles larger than the pores of the woven fabric are dispersed and mixed,
    wherein the liquid silicone rubber permeates into the pores of the woven fabric by the weight thereof and is cured such that the silicone rubber is anchored and coupled to the woven fabric, and
    an electrically conductive layer having electrical conductivity is formed as the electrically conductive particles are caught on the pores of the woven fabric at an interface with the woven fabric and increase in density at the interface.

2. The fabric coated with functional silicone rubber of claim 1, wherein the coating layer is formed by dispersing and mixing electrically conductive wires together with the electrically conductive particles in the liquid silicone rubber and curing the liquid silicone rubber.

3. The fabric coated with functional silicone rubber of claim 2, wherein the electrically conductive wires have elasticity and restoring force in a length direction thereof and are irregularly tangled with each other in the silicone rubber.

4. The fabric coated with functional silicone rubber of claim 2, wherein the electrically conductive wires comprise an electrically conductive fiber and electrically conductive fine metal wires and have a spring shape having gaps between turns, a zigzag shape, or a hook shape.

5. The fabric coated with functional silicone rubber of claim 4, wherein the electrically conductive wires have a single fiber, wool, or mesh structure.

6. The fabric coated with functional silicone rubber of claim 1, wherein as the electrically conductive particles move downward in the coating layer, the electrically conductive particles gradually decrease in density in a direction from the interface with the woven fabric toward a surface of the coating layer such that the surface of the coating layer has no or low electrical conductivity.

7. The fabric coated with functional silicone rubber of claim 1, wherein the electrically conductive particles have uniform density as a whole up to a surface of the coating layer in a thickness direction of the coating layer except for the electrically conductive layer such that the surface of the coating layer has electrical conductivity.

8. The fabric coated with functional silicone rubber of claim 7, wherein an electrically conductive electrode is formed by coating the surface of the coating layer with electrically conductive liquid silicone rubber in which carbon powder is dispersed and mixed, and curing the electrically conductive liquid silicone rubber.

9. A functional garment comprising a garment fabric, an adhesive pattern for making contact with the skin of a person being attached to an inner side of the garment fabric,
    wherein the fabric comprises: a woven fabric made by weaving and comprising uniform pores therein; and a coating layer formed by coating a surface of the woven fabric with liquid silicone rubber in which electrically conductive particles and electrically conductive wires larger than the pores of the woven fabric are dispersed and mixed,
    wherein the liquid silicone rubber permeates into the pores of the woven fabric by the weight thereof and is cured such that the silicone rubber is anchored and coupled to the woven fabric,
    wherein the electrically conductive wires have elasticity and restoring force in a length direction thereof and are irregularly tangled in the silicone rubber.

* * * * *